(12) United States Patent
Keating et al.

(10) Patent No.: US 11,058,355 B2
(45) Date of Patent: *Jul. 13, 2021

(54) DENTAL APPLIANCE FOR USE IN SUPPORTING SENSING DEVICES WITHIN AN ORAL CAVITY

(71) Applicant: KLAB LLC, Henderson, NV (US)

(72) Inventors: Ryan Keating, Henderson, NV (US); Tom Keating, Henderson, NV (US)

(73) Assignee: KLAB LLC, Henderson, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/680,941

(22) Filed: Nov. 12, 2019

(65) Prior Publication Data

US 2020/0163620 A1    May 28, 2020

Related U.S. Application Data

(63) Continuation of application No. 15/730,281, filed on Oct. 11, 2017, now Pat. No. 10,499,852, which is a
(Continued)

(51) Int. Cl.
*A61C 5/70* (2017.01)
*A61B 5/00* (2006.01)
(Continued)

(52) U.S. Cl.
CPC .......... *A61B 5/682* (2013.01); *A61B 5/14539* (2013.01); *A61B 5/4547* (2013.01);
(Continued)

(58) Field of Classification Search
CPC ... A61B 5/682; A61B 5/14539; A61B 5/4547; A61C 5/70; A61C 8/005; A61C 2204/005
See application file for complete search history.

(56) References Cited

U.S. PATENT DOCUMENTS 5,873,721 A    2/1999  Willoughby
2007/0106138 A1    5/2007  Beiski et al.
(Continued)

OTHER PUBLICATIONS

Li et al., Sensor-Embedded Teeth for Oral Activity Recognition, Department of Computer Science and Information Engineering, Department of Electrical Engineering, 4 pages, National Taiwan University, Taipei, Taiwan.
(Continued)

*Primary Examiner* — Heidi M Eide
*Assistant Examiner* — Drew S Folgmann
(74) *Attorney, Agent, or Firm* — Howard & Howard Attorneys PLLC

(57) ABSTRACT

A dental appliance is described herein. The dental appliance includes an abutment device adapted to be coupled to a jawbone and a sensor support assembly coupled to the abutment device. The sensor support assembly includes a sensor chamber that is configured to receive a sensing device therein. A chamber cover is coupled to the sensor support assembly to enclose the sensor chamber. The chamber cover includes a plurality of orifices that are configured to couple the sensor chamber in flow communication with an oral cavity. A tooth cap is coupled to the abutment device and includes a cap opening to receive the sensor support assembly therein.

17 Claims, 16 Drawing Sheets

Related U.S. Application Data continuation of application No. 14/829,481, filed on Aug. 18, 2015, now Pat. No. 9,814,427.

(60) Provisional application No. 62/038,587, filed on Aug. 18, 2014.

(51) Int. Cl.
*A61C 8/00* (2006.01)
*A61B 5/145* (2006.01)

(52) U.S. Cl.
CPC ............... *A61C 5/70* (2017.02); *A61C 8/005* (2013.01); *A61C 2204/005* (2013.01)

(56) References Cited

U.S. PATENT DOCUMENTS

| | | |
|---|---|---|
| 2009/0286202 A1 | 11/2009 | Ford et al. |
| 2010/0143871 A1 | 6/2010 | Berger |
| 2012/0172678 A1 | 7/2012 | Logan et al. |
| 2012/0300908 A1* | 11/2012 | Mayer .................. A61B 6/425 378/168 |
| 2012/0300961 A1 | 11/2012 | Moeller |
| 2015/0170504 A1 | 6/2015 | Jooste |

OTHER PUBLICATIONS

Igor et al., Nano sensors integrated into dental implants for detection of acute myocardial infarction, International Journal of Emerging Trends & Technology in Computer Science, Jul.-Aug. 2012, pp. 85-87, vol. 1, Issue 2.

* cited by examiner

DENTAL APPLIANCE FOR USE IN SUPPORTING SENSING DEVICES WITHIN AN ORAL CAVITY

CROSS-REFERENCE TO RELATED APPLICATION

This application is a continuation of U.S. patent application Ser. No. 15/730,281, filed Oct. 11, 2017, which is a continuation of U.S. patent application Ser. No. 14/829,481, filed Aug. 18, 2015 (now U.S. Pat. No. 9,814,427, issued Nov. 14, 2017), which claims priority to U.S. Provisional Patent Application Ser. No. 62/038,587, filed Aug. 18, 2014, the disclosures of which are hereby incorporated by reference in their entirety.

TECHNICAL FIELD

The subject matter disclosed herein relates generally to dental appliances, and more particularly, to a dental appliance for use with sensing devices including bacteria sensors and/or pH sensors for sensing a pH level of saliva contained within an oral cavity.

BACKGROUND OF THE INVENTION

Dental plaque is a biofilm that forms naturally on teeth between brushing and dental visits. Dental plaque can be a precursor to more severe oral health problems including: dental caries, tooth decay, gingivitis, and chronic periodontitis. The occurrence of dental cavities, gingivitis, and dental calculus are some of the most common systemic diseases of the body. In addition, oral diseases have been shown to be an indicator of additional health problems such as high blood pressure, hypertension, and some cancers. Consequently, dental practitioners are in need of an adequate means to monitor and control the development of these oral diseases.

The oral cavity of the human body naturally produces saliva to facilitate the breakdown of food during mastication. The saliva produced in the oral cavity may experience significant changes in pH levels. Changes in the pH levels of saliva within the oral cavity may significantly affect overall oral heath including causing an increase in tooth decay and the formation of dental cavities.

At least some known oral pH sensors require substantially large dental devices that must be secured within the patient's mouth causing significant discomfort and distress for the patients. As such, it is desirable to provide a dental appliance that facilitates supporting sensing devices within the oral cavity and reducing the discomfort experience by the patient, thereby improving the overall health of the patient. The present invention is aimed at the problem identified above.

SUMMARY OF THE INVENTION

In one aspect of the present invention, a dental appliance for use in positioning a sensing device within an oral cavity is provided. The dental appliance includes a sensor assembly and a tooth cap. The sensor assembly includes a support member and a sensor support assembly extending outwardly from the support member. The sensor support assembly includes a recessed portion that defines a sensor chamber that is configured to receive the sensing device therein. The tooth cap is coupled to the sensor assembly and adapted to be positioned within the oral cavity and orientated along a biting surface.

In another aspect of the present invention, a dental appliance for use in positioning a sensor device within an oral cavity is provided. The dental appliance includes an abutment device adapted to be coupled to a jawbone, a sensor assembly, and a tooth cap. The sensor assembly includes a support member that is coupled to the abutment device and a sensor support assembly extending outwardly from the support member. The sensor support assembly includes a recessed portion that defines a sensor chamber that is configured to receive the sensing device therein. The tooth cap is coupled to the sensor assembly and positioned within the oral cavity and orientated along a biting surface.

In yet another aspect of the present invention, a dental appliance for use in positioning a sensing device within an oral cavity is provided. The dental appliance includes a support member that is adapted to be coupled to a jawbone, an abutment device that is removably coupled to the support member and extending outwardly from the jawbone, and a sensor assembly coupled to the abutment device. The sensor assembly includes a support member coupled to an outer surface of the abutment device, a sensor support assembly that is coupled to the support member, and a chamber cover. The sensor support assembly includes a recessed portion having an interior surface defining a sensor chamber therein. The sensor chamber configured to receive a sensor therein to facilitate supporting the sensor within the sensor chamber. The chamber cover is removably coupled to the sensor support assembly to enclose the sensor chamber. The chamber cover has a plurality of orifices extending through the chamber cover to couple the sensor chamber in flow communication with the oral cavity. A tooth cap is removably coupled to the abutment device. The tooth cap has an inner surface and an outer surface. The inner surface defines a cavity that is configured to receive the abutment device therein. The outer surface includes an opening that extends through the tooth cap. The opening is configured to receive the sensor support assembly therein such that an outer surface of the chamber cover is substantially flush with the tooth cap outer surface.

In another aspect of the present invention, a dental appliance for use in positioning a sensing device within an oral cavity is provided. The dental appliance includes an abutment device and a tooth cap. The abutment device is adapted to be removably coupled a jawbone and extends outwardly from the jawbone into the oral cavity. The abutment device includes a support member and a sensor support assembly that extends outwardly from an outer surface of the support member. The sensor support assembly includes a recessed portion having an interior surface that defines a sensor chamber therein. The sensor chamber is configured to receive a sensor therein to facilitate supporting the sensor within the sensor chamber. A chamber cover is removably coupled to the sensor support assembly and is configured to enclose the sensor chamber. The chamber cover has a plurality of orifices extending through the chamber cover to couple the sensor chamber in flow communication with the oral cavity. The tooth cap is removably coupled to the abutment device. The tooth cap has an inner surface and an outer surface. The inner surface defines a cavity that is configured to receive the support member therein. The outer surface includes an opening that extends through the tooth cap and is configured to receive the sensor support assembly therein such that an outer surface of the chamber cover is substantially flush with the tooth cap outer surface.

In yet another aspect of the present invention, a dental appliance for use in supporting a sensing device within an oral cavity is provided. The dental appliance includes a flexible dental tray including an inner surface and an outer surface. The inner surface defines a cavity that is configured to receive at least one tooth therein. A sensor support assembly is coupled to the dental tray for supporting a sensing device from the dental tray. A sensor attachment assembly is removably coupled to the sensor support assembly and a sensing device is coupled to the sensor attachment assembly. The sensor attachment assembly is configured to support the sensing device from the sensor support assembly. In one embodiment, the inner surface of the flexible dental tray includes a recessed portion defining a cavity that is configured to receive the sensor support assembly therein. In another embodiment of the present invention, the sensor support assembly is unitarily formed with the flexible dental tray and extends outwardly from the outer surface of the flexible dental tray.

BRIEF DESCRIPTION OF THE DRAWINGS

Other advantages of the present invention will be readily appreciated as the same becomes better understood by reference to the following detailed description when considered in connection with the accompanying drawings wherein.

Corresponding reference characters indicate corresponding parts throughout the drawings.

DETAILED DESCRIPTION OF THE PREFERRED EMBODIMENT

With reference to the drawings and in operation, the invention overcomes at least some disadvantages of known dental appliances by providing a dental appliance that may be used to support sensing devices within an oral cavity for use in sensing physiological and chemical data of a person and/or animal. For example, the sensing device may include, but is not limited to including, pH sensors, pressure sensors, force sensors, movement sensors, RFID, accelerometers, chemical sensors, and/or any suitable sensing device that may be positioned within an oral cavity of a human and/or animal. More specifically, the invention described herein includes a dental appliance that includes a sensor support assembly that includes a sensor chamber for use in supporting a sensing device therein, and a removable chamber cover to allow access to the sensing device and to enclose the sensing device within the sensor chamber during use. In addition, the chamber cover includes a plurality of orifices extending through the chamber cover to allow the sensor chamber to be coupled in flow communication with the oral cavity. By providing a dental appliance that includes a recessed sensor chamber and a porous chamber cap, a sensing device for obtaining biometric sensor data may be placed within an oral cavity of a patient with minimal discomfort to the patient. In addition, by providing a porous chamber cap, the dental appliance allows for fluid within the oral cavity to contact the sensing device to facility sensing biometric data and facilitates preventing damage to the sensing device during normal masticating activities being performed by the patient, thereby increasing the amount of time the sensing device may be positioned within the oral cavity and the amount of biometric data that may be obtained.

In general, the present invention is aimed at dental appliances that may be used to replace one or more existing teeth within a patient's oral cavity. The dental appliance is adapted to replace all, or a portion of, one or more existing teeth to enable a patient to obtain a normalized bite to facilitate improving the movement and function of the patients teeth, gum, and/or jaw.

A selected embodiment of the invention will now be explained with reference to the drawings. It will be apparent to those skilled in the art from this disclosure that the following description of the embodiment of the invention is provided for illustration only and not for the purpose of limiting the invention as defined by the appended claims and their equivalents.

Figure 1:
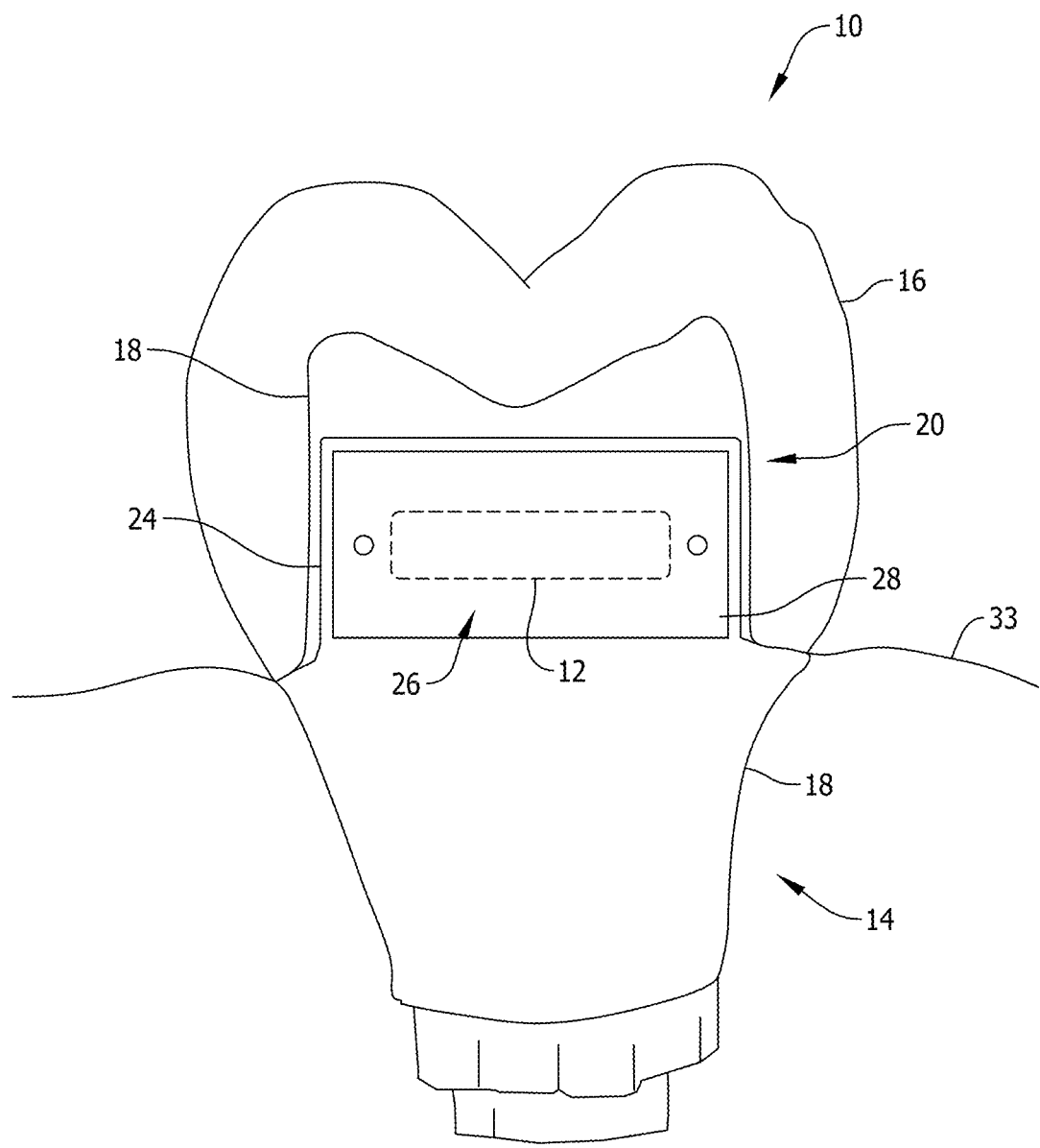
FIG. 1 is a schematic view of a dental appliance for use in supporting sensing devices within an oral cavity, according to an embodiment of the present invention.
Figure 2:
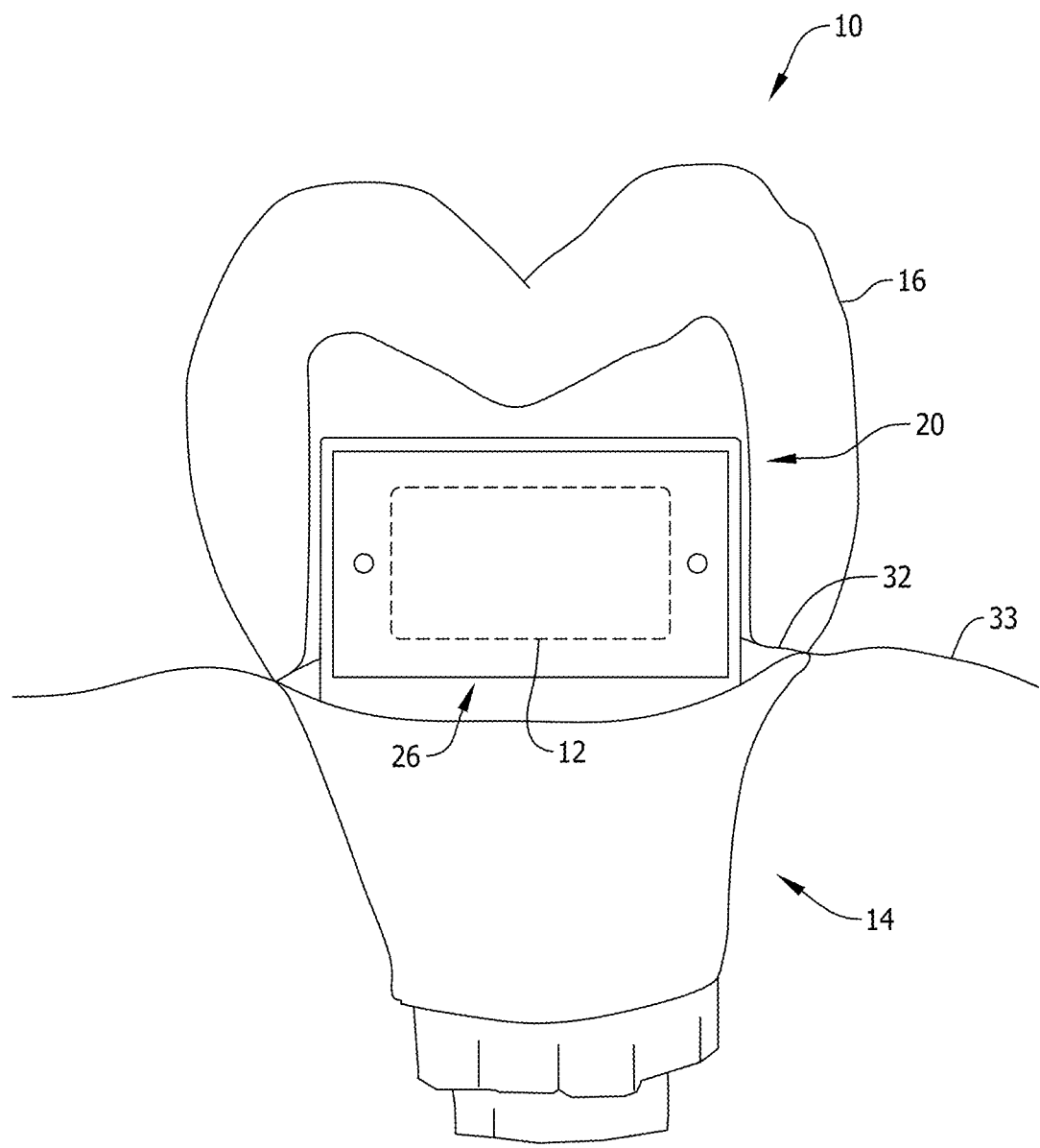
FIGS. 2 and 3 are additional schematic views of the dental appliance shown in FIG. 1.
Figure 3:
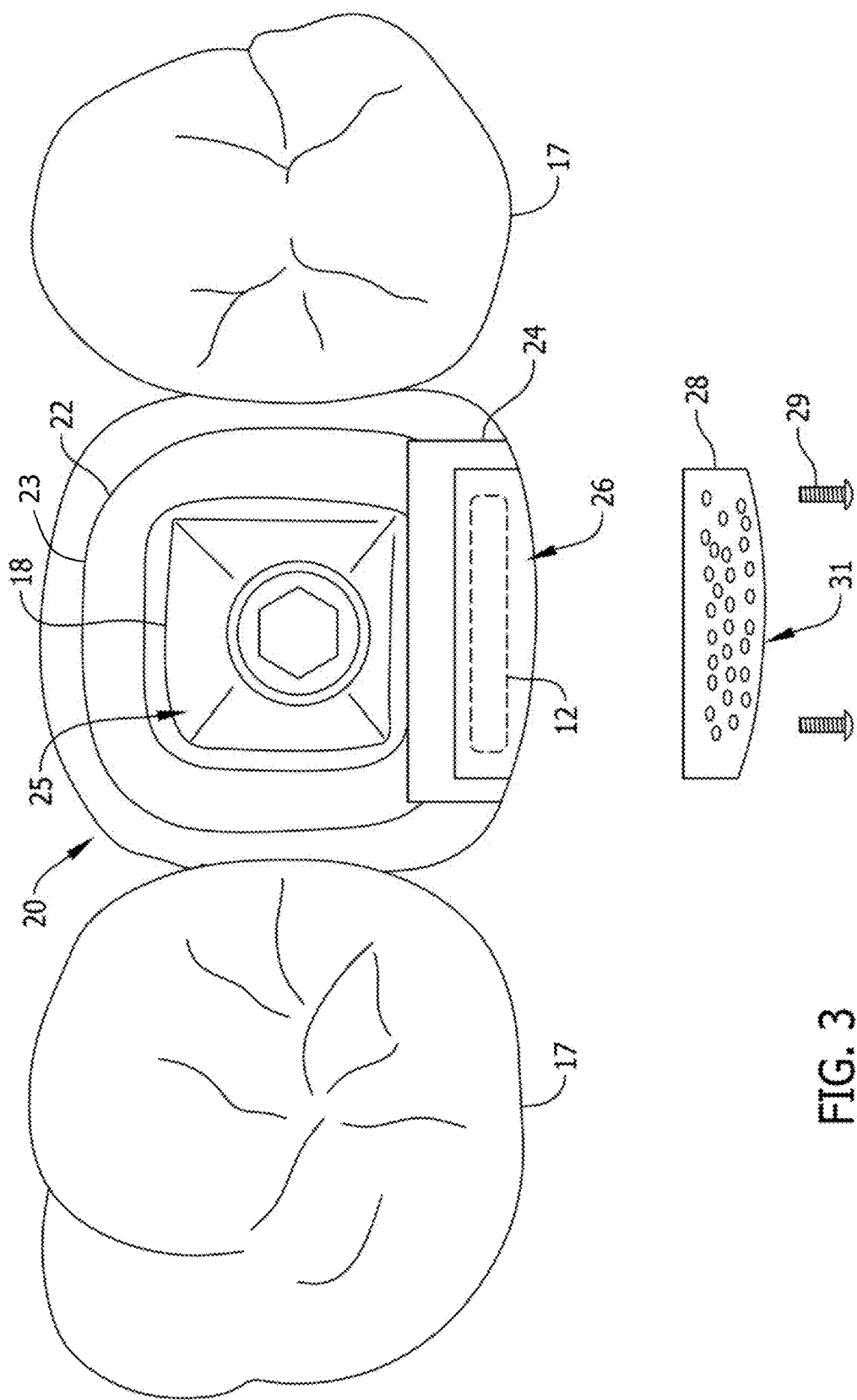
Figure 4:
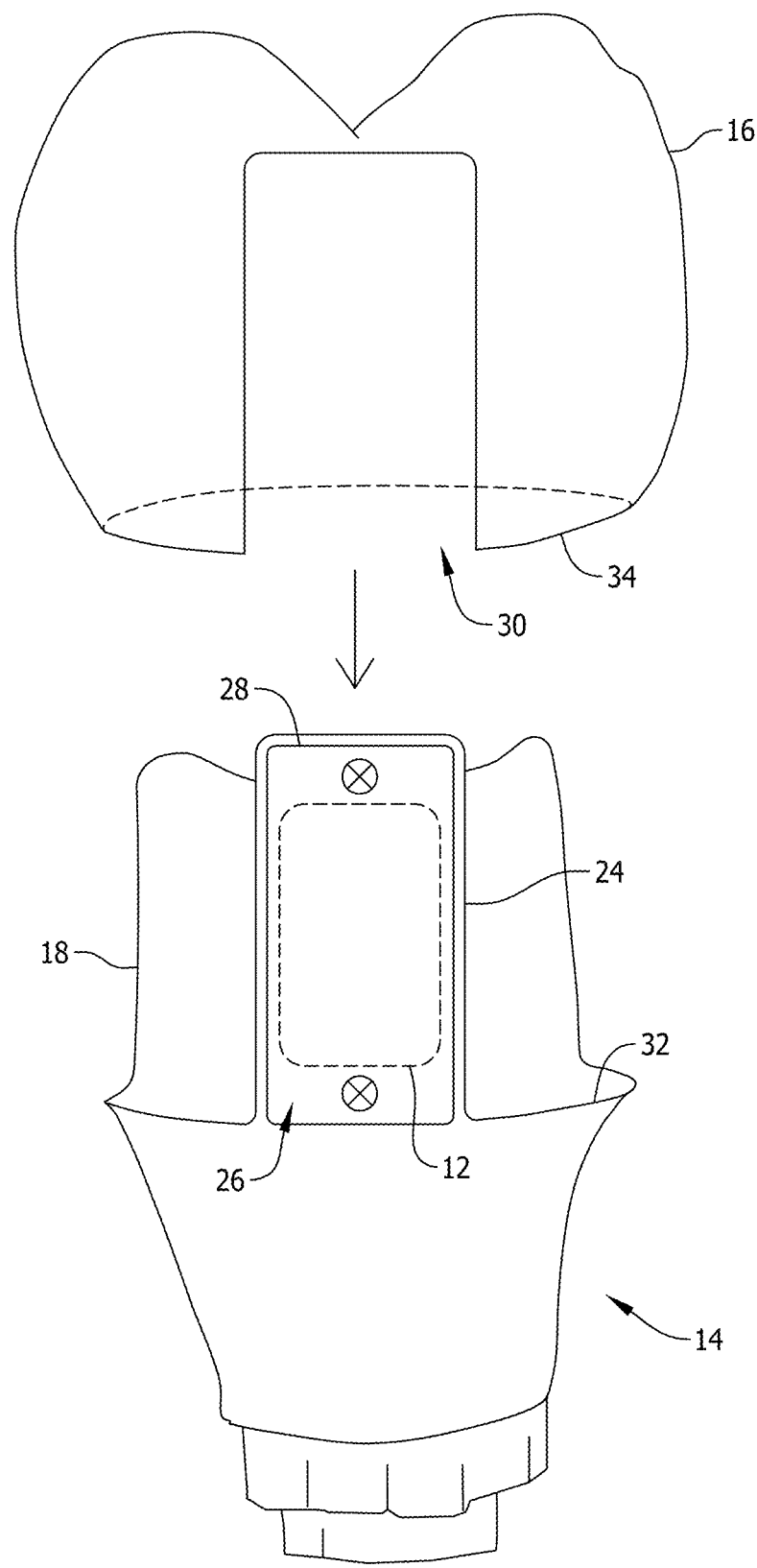
FIG. 4 is an exploded schematic view of the dental appliance shown in FIG. 1.
Figure 5:
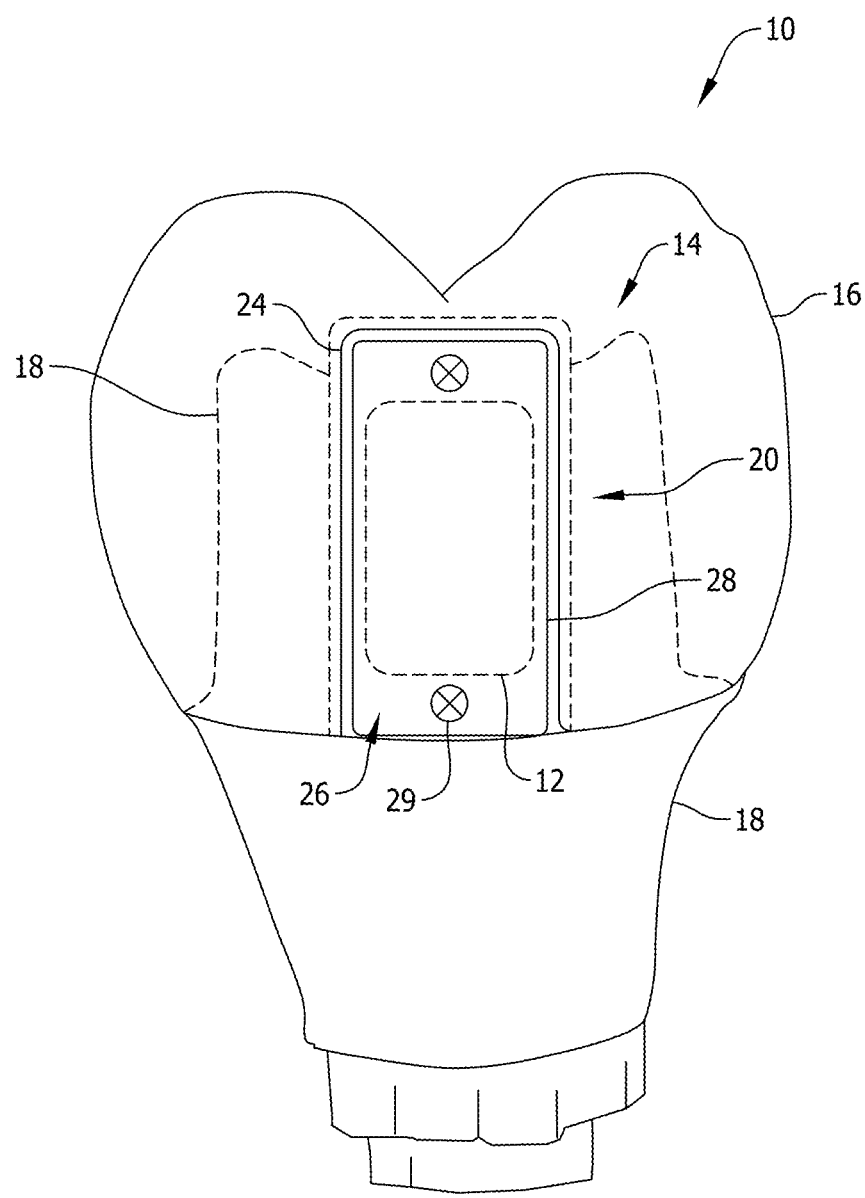
FIGS. 5-7 are additional schematic views of the dental appliance shown in FIG. 1.

FIG. 1 is a schematic view of a dental appliance 10 for use in supporting sensing devices 12 within an oral cavity, according to an embodiment of the present invention. FIGS. 2-12 are additional views of the dental appliance 10. In the illustrated embodiment, the dental appliance 10 is configured to replace one or more teeth positioned within an oral cavity of a patient. In one embodiment, the dental appliance 10 is adapted to be coupled to a jawbone of a patient and extend outwardly from the jawbone and orientated with respect to one or more existing teeth within a patient's mouth. In the illustrated embodiment, the dental appliance 10 includes a contoured outer surface to simulate one or more existing teeth positioned within the patient's mouth. In addition, the dental appliance 10 is configured to provide sufficient bite support to enable the patient to perform normal oral functions with the dental appliance 10 positioned within the oral cavity. In one embodiment, the outer surface of the dental appliance may be substantially similar to an existing tooth that was removed from the patient's jaw to facilitate replacing the tooth with the dental appliance 10. In one embodiment, the dental appliance 10 may be configured to be coupled to an existing tooth. For example, a portion of the surface area of an existing tooth may be reduced to accommodate the dental appliance 10 being placed over the existing tooth and coupled to the existing tooth to form a row of teeth.

In the illustrated embodiment, the dental appliance 10 includes an abutment assembly 14 and a tooth cap 16. In one embodiment, the abutment assembly 14 is configured to be removably coupled to a jawbone of a patient and extend outwardly from the jawbone into the oral cavity. The abutment assembly 14 is orientated with respect to existing teeth to form a portion of a patient's biting surface. In one embodiment, the dental appliance 10 may include an anchoring member (not shown) that may be embedded and/or coupled to the jawbone. The abutment assembly 14 is removably coupled to the anchoring member to facilitate supporting the abutment assembly 14 from the jawbone. In another embodiment, the abutment assembly 14 may include an inner surface that defines a cavity that is sized and shaped to receive an existing tooth 17 (shown in FIG. 13) therein to facilitate supporting the abutment assembly 14 from the existing tooth 17. For example, in one embodiment, the surface area of an existing tooth 17 may be removed to reduce a cross-sectional area of the existing tooth to allow the abutment assembly 14 to be positioned over the existing tooth.

In the illustrated embodiment, the abutment assembly 14 includes an abutment device 18 and a sensor assembly 20 that is coupled to the abutment device 18. The sensor assembly 20 includes a support member 22 and a sensor support assembly 24 that is coupled to the support member 22. The sensor assembly 20 may be sized and shaped to extend across a space in the bite line vacated by one or more teeth. The support member 22 is coupled to an outer surface of the abutment device 18 to facilitate supporting the sensor support assembly 24 from the abutment device 18. In one embodiment, the support member 22 includes a support ring 23 having an inner surface that defines an opening 25 (shown in FIGS. 3 and 10-14) that is sized and shaped to receive a portion of the abutment device 18 therethrough. In another embodiment, the sensor assembly 20 does not include the support member 22 and the sensor support assembly 24 is coupled to the abutment device 18.

In the illustrated embodiment, the sensor support assembly 24 extends outwardly from the support member 22 and includes a recessed portion that includes an inner surface that defines a sensor chamber 26 therein. The sensor chamber 26 is sized and shaped to receive the sensing device 12 therein to facilitate supporting the sensing device 12 within the sensor chamber 26. The dental appliance 10 also includes a chamber cover 28 that is configured to be removably coupled to the sensor support assembly 24 to enclose sensing device 12 within the sensor chamber 26. In one embodiment, the chamber cover 28 may be removably coupled to the sensor support assembly 24 with one or more fastening members 29 such as, for example screws and/or an adhesive. In another embodiment, the dental appliance 10 may not include the chamber cover 28. In addition, the dental appliance 10 may include a sensing device tray (not shown) that may be placed within the sensor chamber 26 and removably coupled to the sensor support assembly 24 to facilitate supporting the sensing device 12 from the sensor support assembly 24. Moreover, in one embodiment, the sensing device 12 may be coupled to the sensing device tray with an adhesive and/or one or more fastening members.

In the illustrated embodiment, the chamber cover 28 may include a porous outer surface to allow the sensor chamber 26 to be coupled in flow communication with the surrounding oral cavity. For example, in one embodiment, the chamber cover 28 may include a plurality of orifices 31 extending through the chamber cover 28 to allow fluid and/or air to flow through the chamber cover 28 and between the sensor chamber 26 and the oral cavity to enable the sensing device 12 to contact the fluid and/or air being contained within the oral cavity.

Figure 6:
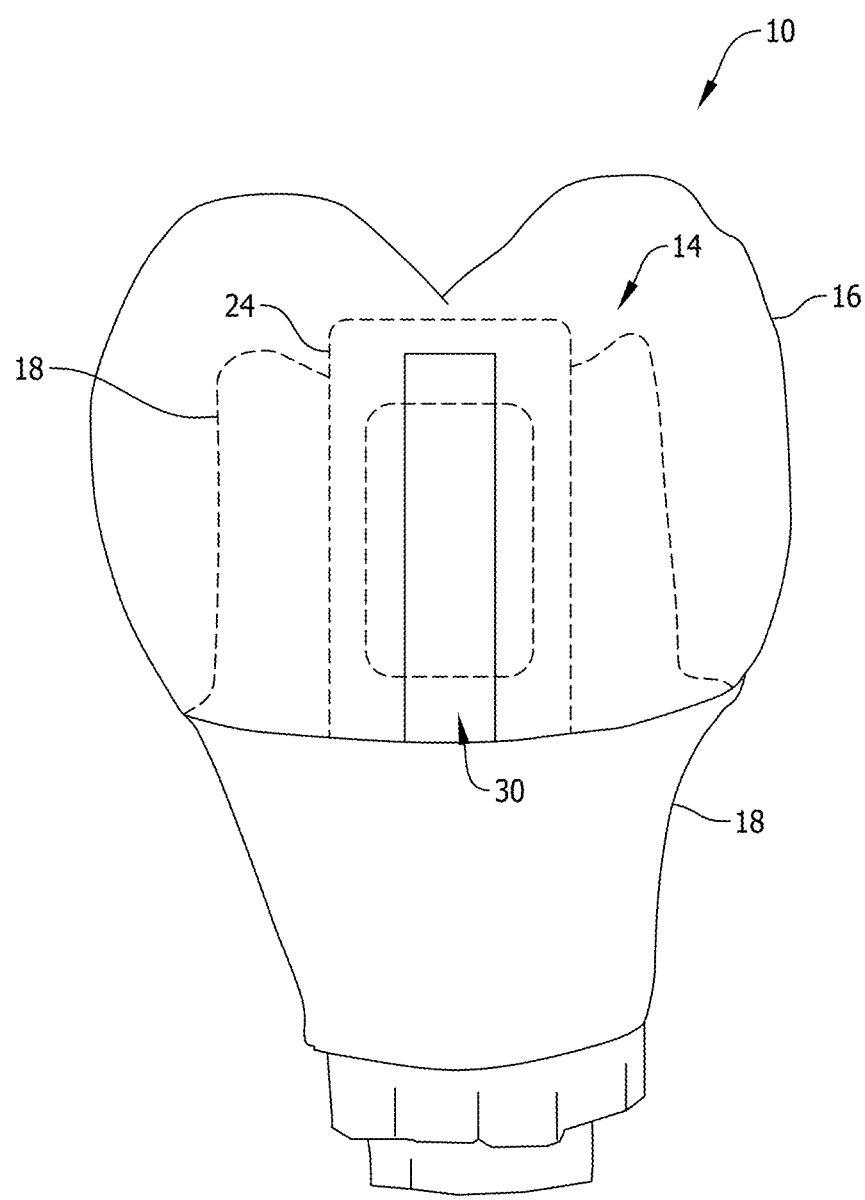

The tooth cap 16 is adapted to be removably coupled to the abutment device 18 to form at least a portion of the outer surface of the dental appliance. In addition, the tooth cap 16 includes a contoured outer surface that is sized and shaped to simulate the surrounding existing teeth 17 and to facilitate forming a natural biting surface of the patient. The tooth cap 16 also includes an inner surface that defines a cavity that is configured to receive the abutment device 18 therein. The outer surface of the tooth cap 16 includes a cap opening 30 that extends through the tooth cap 16. The cap opening 30 is sized and shaped to receive the sensor support assembly 24 therein such that the outer surface of the chamber cover 28 is substantially flush with the tooth cap outer surface. In one embodiment, the tooth cap outer surface may overlap a portion of the sensor chamber 26 and/or the chamber cover 28 to facilitate securing the chamber cover 28 and/or the sensing device 12 within the sensor chamber 26. For example, in one embodiment, the sensor assembly 20 may not include the chamber cover 28. The tooth cap 16 outer surface may extend across all, or a portion of, the sensor chamber 26 to facilitate supporting the sensing device 12 within the sensor chamber 26, as shown in FIG. 6. In one embodiment, the cap opening 30 may be sized and shaped to couple the sensor chamber 26 in flow communication with the oral cavity. In another embodiment, the tooth cap 16 may not include a cap opening 30. In addition, the tooth cap 16 may include a porous region extending across the sensor chamber 26 and/or one or more orifices extending through the tooth cap 16 and orientated with respect to the sensor chamber 26 to facilitate channeling air/fluid between the sensor chamber 26 and the oral cavity.

In one embodiment, the abutment device 18 may include a supporting ridgeline 32 that is positioned at or below the patient gumline 33. In addition, the tooth cap 16 may include a corresponding outer ridge 34 that is configured to contact the supporting ridgeline 32 of the abutment device 18 to facilitate supporting the tooth cap 16. In the illustrated embodiment, the tooth cap 16 and the abutment assembly 14 include corresponding openings that are each sized and shaped to receive a fastening assembly therein to facilitate removably coupling the tooth cap 16 to the abutment assembly 14.

In one embodiment, during installation of the dental appliance 10, a dentist and/or oral surgeon may place the sensing device 12 within the sensor chamber, secure the chamber cap to the abutment device, attach the abutment device to the jawbone and/or existing tooth, and coupled the tooth cap to the abutment device. During use, the sensing device may sense the chemistry composition and/or pH levels of saliva, fluid, air, and/or material within the patient's oral cavity during normal oral operations.

Figure 7:
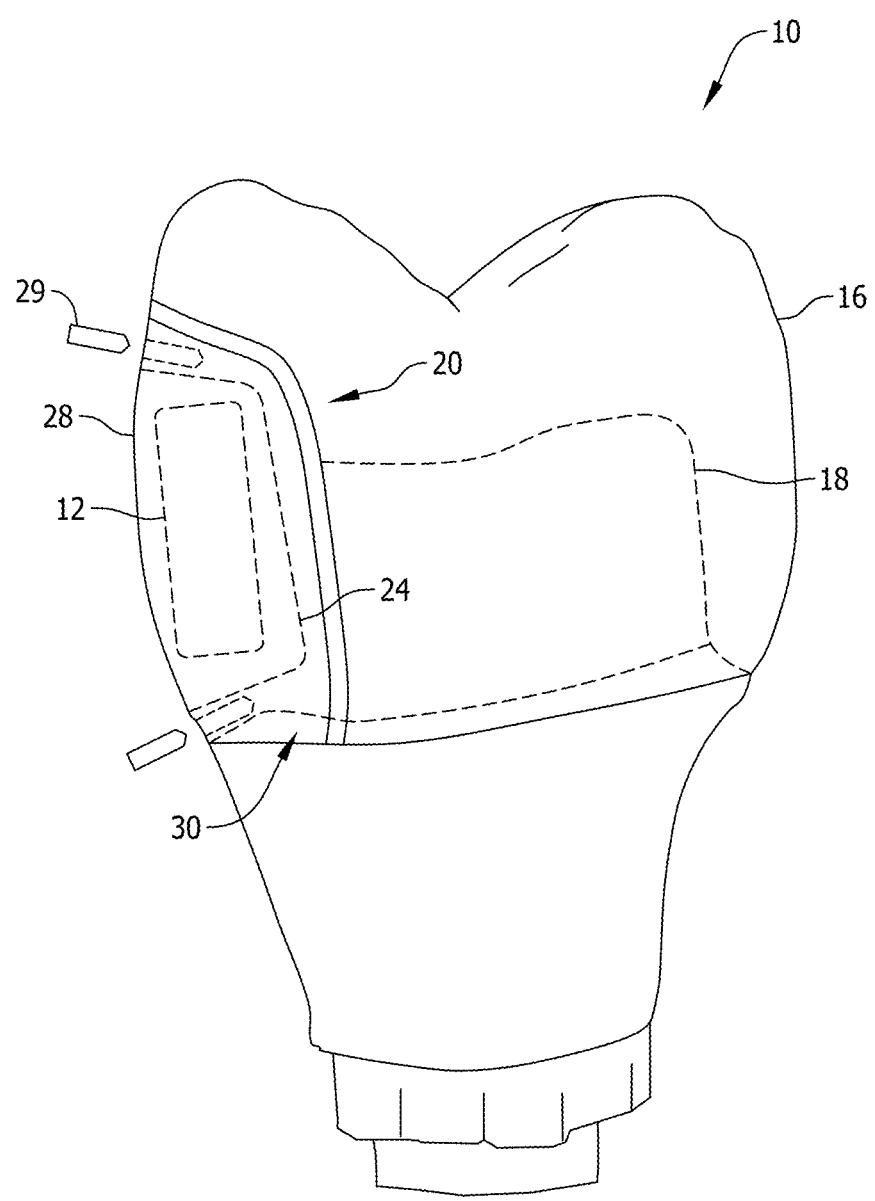
Figure 8:
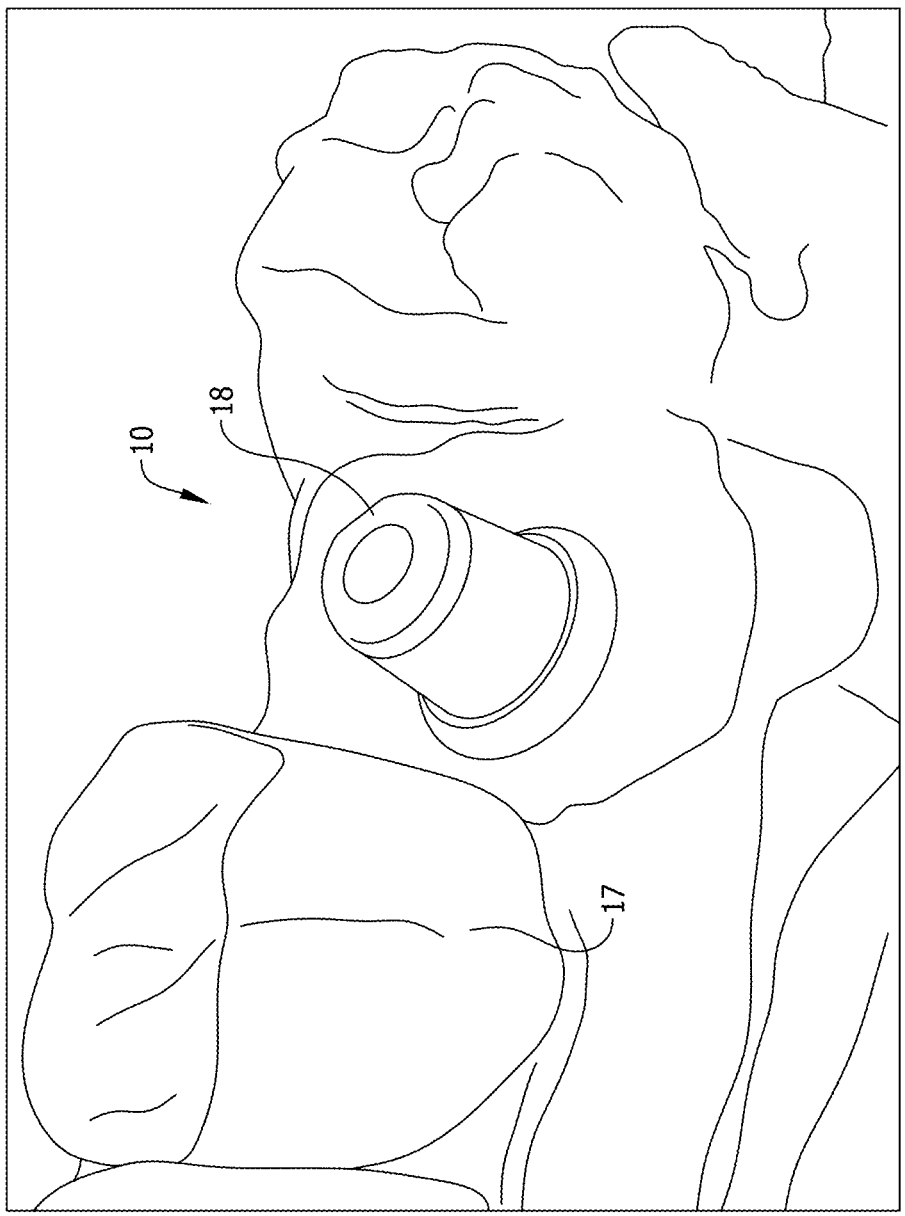
FIGS. 8-12 are perspective views of portions of the dental appliance shown in FIG. 1, according to an embodiment of the present invention.
Figure 9:
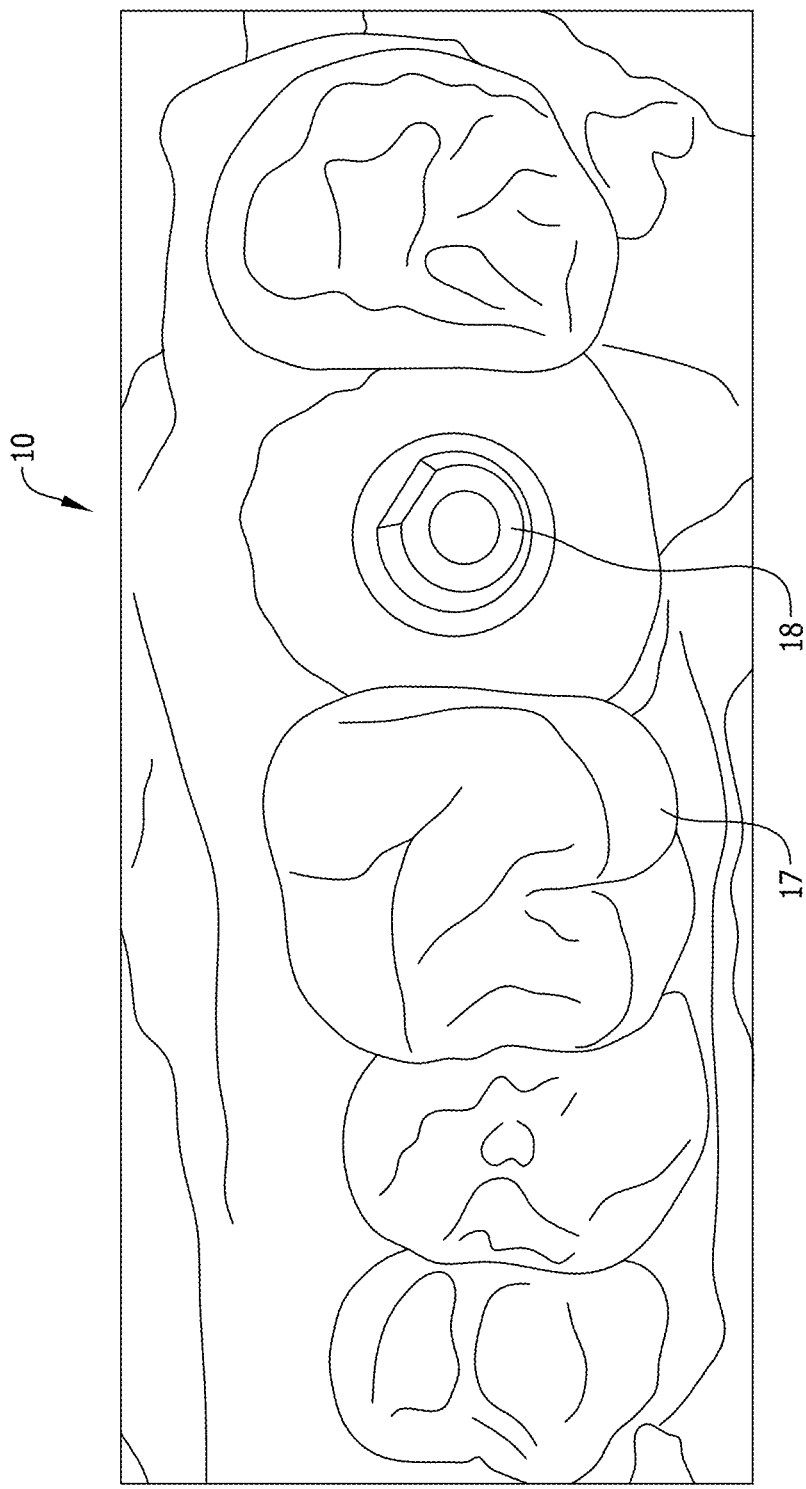
Figure 10:
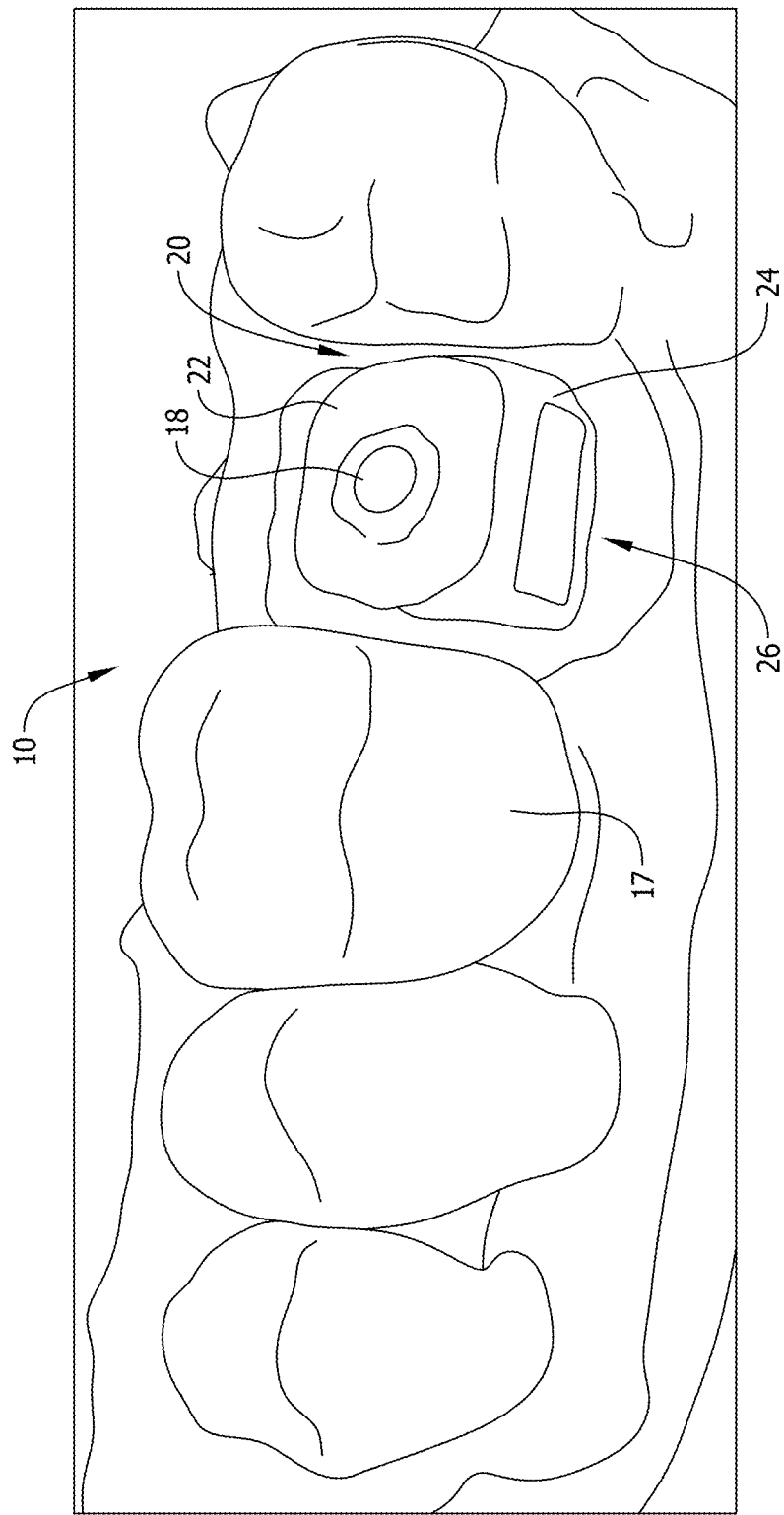
Figure 11:
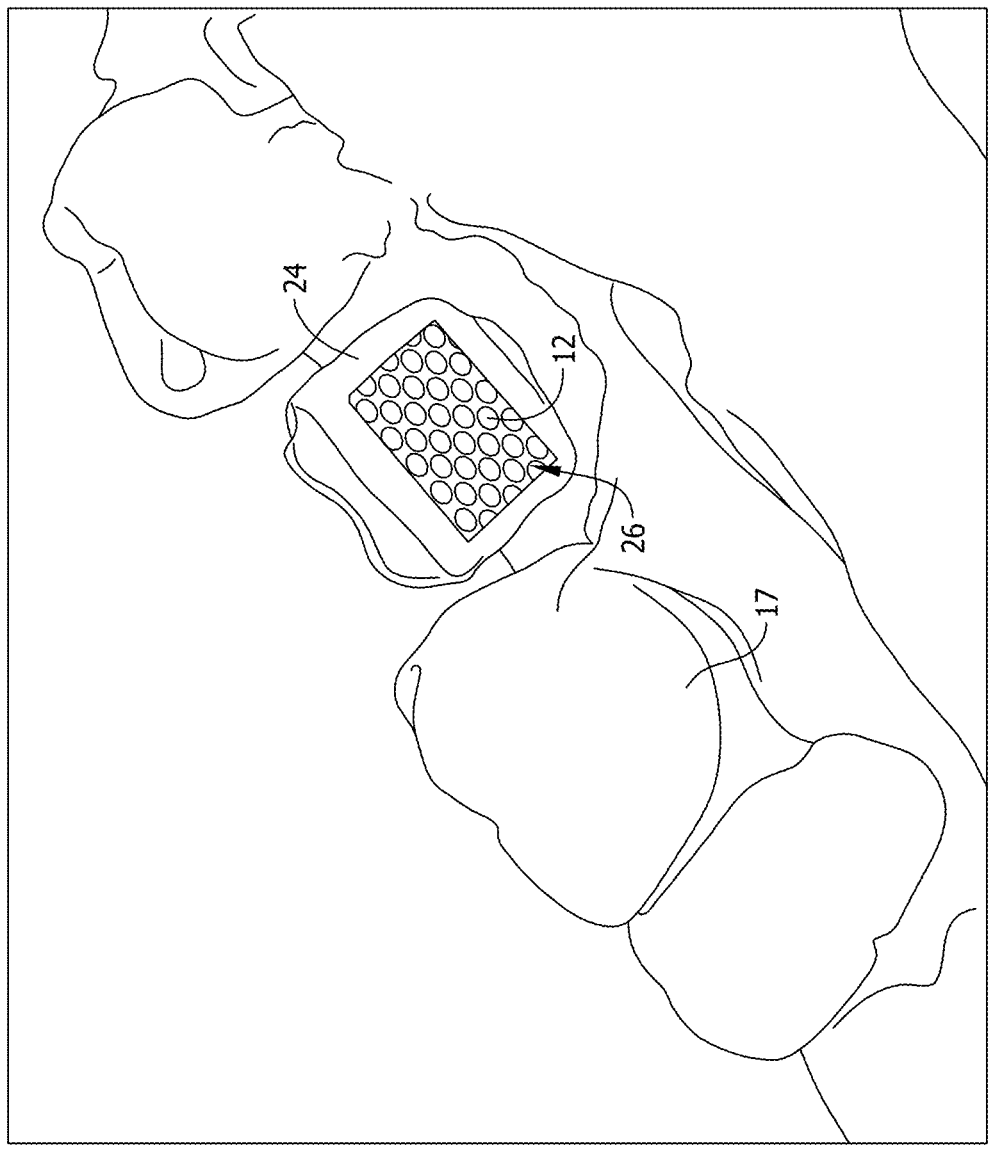
Figure 12:
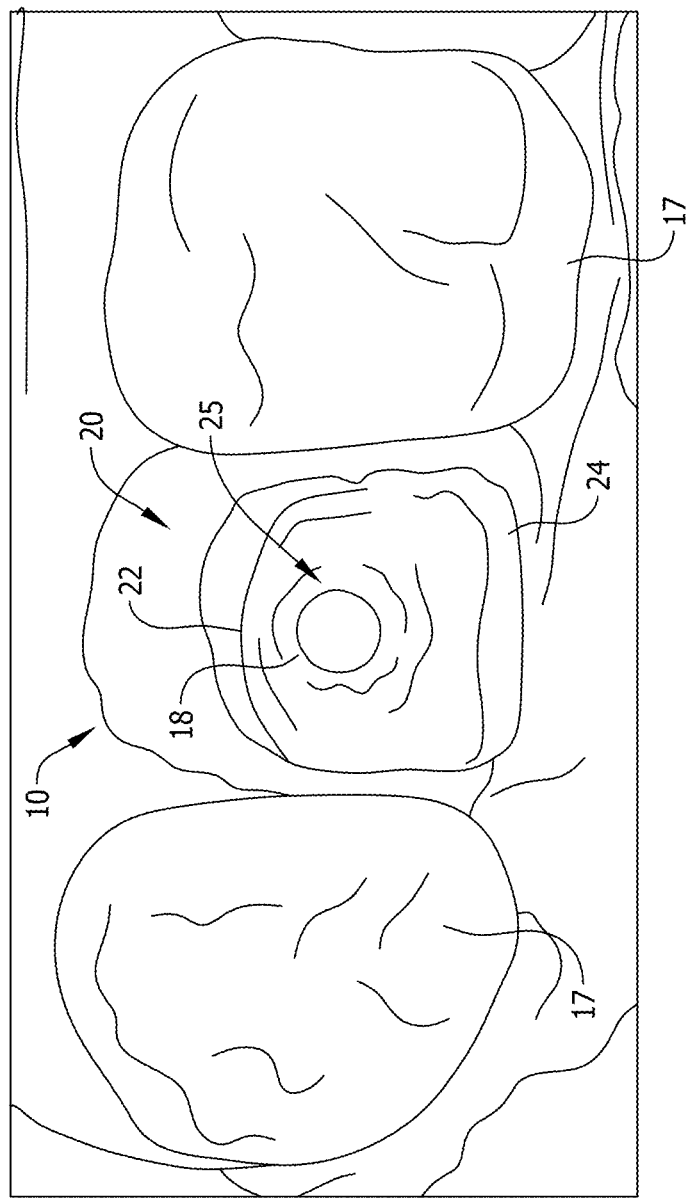

FIG. 7 shows a side view of the dental appliance 10 including an upper molar abutment and crown, according to an embodiment of the present invention. The abutment is fabricated to maximize the buccal surface of upper molars for placement of sensor and/or a microchip device. The chip platform can be altered depending on size of chip and tissue contour. Also, sensor/microchip could be screwed in place or bonded. The edges of chip would be clear of tissue and restoration margins. Any popular restoration could be screw retained or cemented to abutments. Abutments could be fabricated using titanium or zirconia with any widely used restoration material (Emax, PFM, Zirconia, etc. . . . ).

Figure 13:
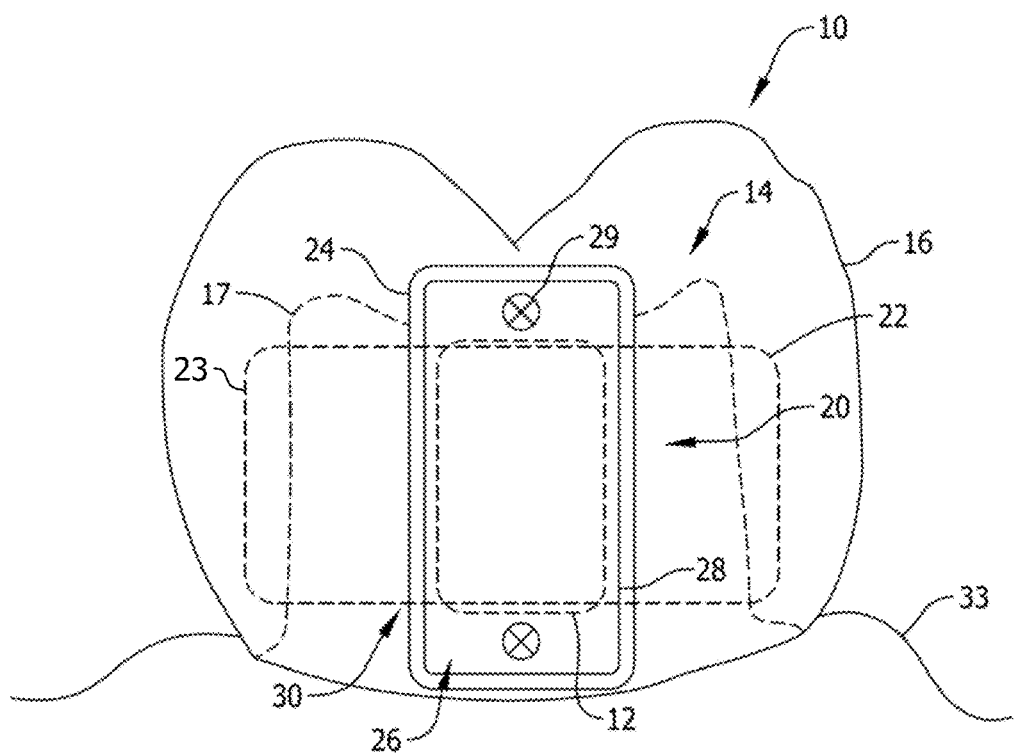
FIG. 13 is another schematic view of the dental appliance, according to an embodiment of the present invention.
Figure 14:
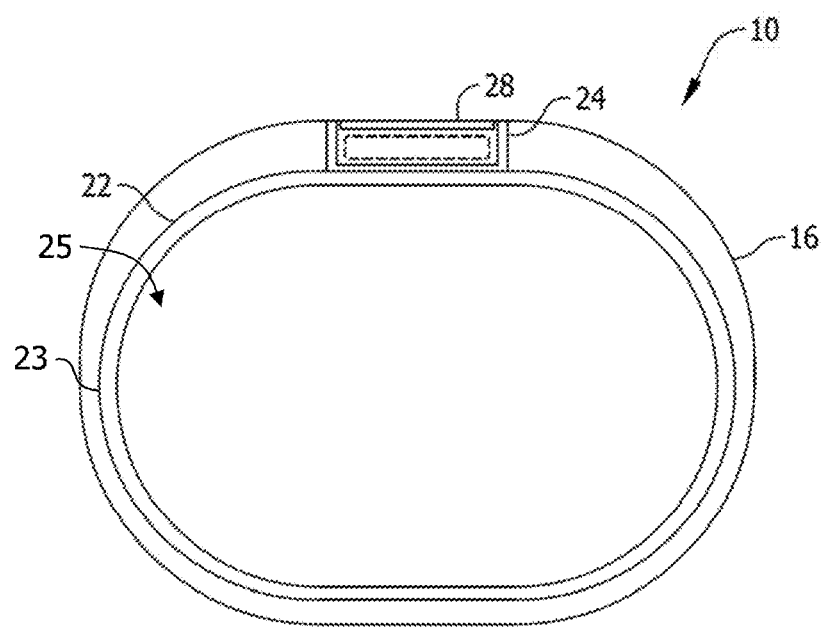
FIG. 14 is another bottom view of the dental appliance shown in FIG. 13, according to an embodiment of the present invention.

FIG. 13 is a schematic view of the dental appliance 10, according to another embodiment of the present invention. FIG. 14 is a bottom view of the dental appliance 10 shown in FIG. 13. In the illustrated embodiment, the dental appliance 10 includes a sensor assembly 20 and a tooth cap 16 that is coupled to the sensor assembly 20. The sensor assembly 20 includes a support member 22 that is sized and shaped to receive a portion of an existing tooth therethrough to facilitate coupling the dental appliance 10 to the existing tooth 17. For example, a portion of the outer surface of the existing tooth 17 may have been removed and shaped to facilitate coupling the support member 22 to the existing tooth outer surface. In one embodiment, the support member 22 includes a support ring 23 that extends extending about a circumference of the at least one existing tooth.

In the illustrated embodiment, the sensor assembly 20 includes a sensor support assembly 24 that extends outwardly from the support member 22. The sensor support assembly 24 includes a recessed portion defining a sensor chamber 26 that is configured to receive a sensing device 12 therein. The tooth cap 16 is coupled to the sensor assembly 20 and is adapted to be positioned within the oral cavity and orientated along a biting surface formed by adjacent teeth. In one embodiment, the tooth cap 16 may include at least one opening and/or orifice that extends through an outer surface of the tooth cap 16 to couple the sensor chamber 26 in flow communication with the oral cavity.

The sensor assembly 20 may also include a chamber cover 28 that is removably coupled to the sensor support assembly 24 to enclose the sensor chamber 26. In addition, the chamber cover 28 may include at least one orifice 31 (shown in FIG. 3) that extends through the chamber cover 28 to couple the sensor chamber 26 in flow communication with the oral cavity to allow the sensing device 12 to contact the fluid and/or air present in the oral cavity. In another embodiment, the tooth cap 16 may include a cap opening 30 that extends through the tooth cap 16. The cap opening 30 is sized and shaped to receive the sensor support assembly 24 therein, such that an outer surface of the chamber cover 28 is substantially flush with the tooth cap outer surface.

Figure 15:
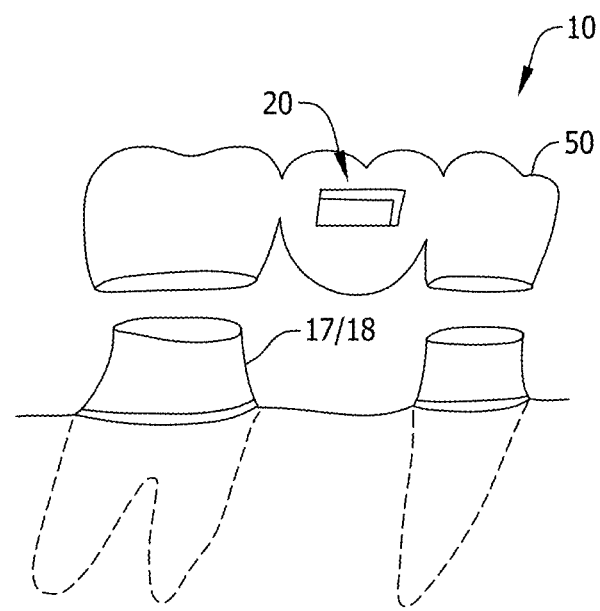
FIGS. 15-17 are additional views of the dental appliance shown in FIGS. 1 and 13, according to an embodiment of the present invention.
Figure 16:
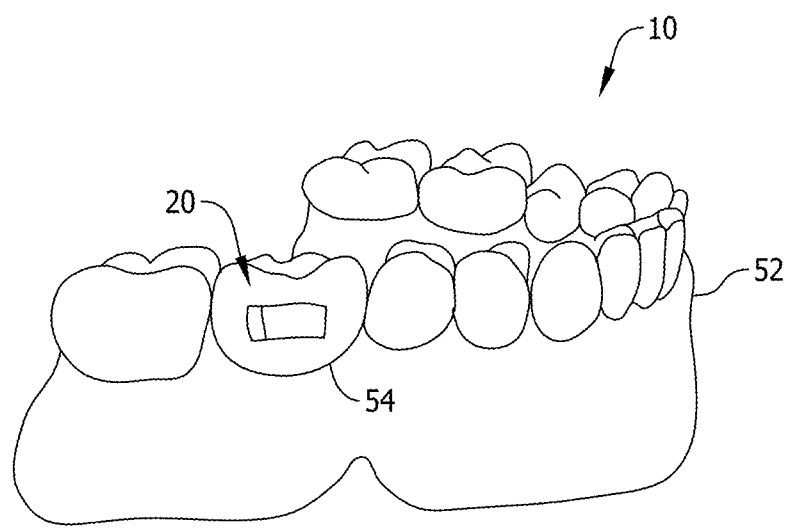
Figure 17:
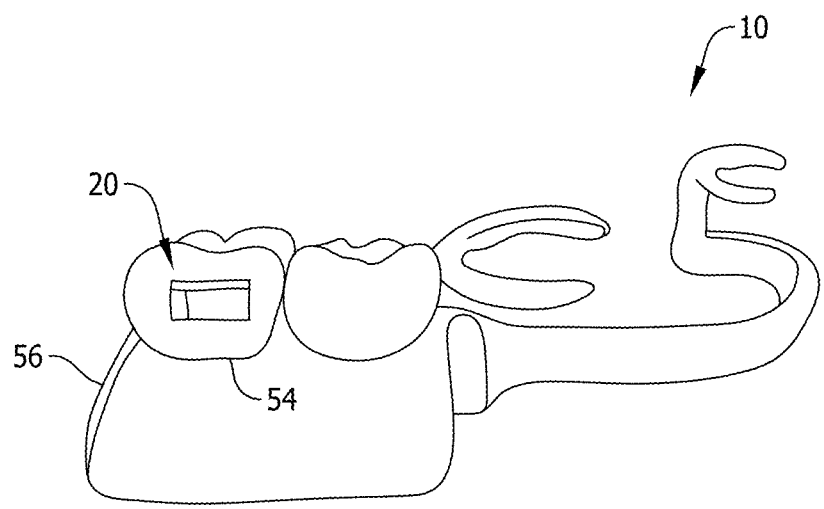

FIGS. 15-17 are additional schematic views of the dental appliance 10, according to embodiments of the present invention. Referring to FIG. 15, in one embodiment, the dental appliance 10 may include a fixed dental bridge 50 including the sensor assembly 20. The sensor assembly 20 is coupled to the fixed dental bridge 50 to facilitate supporting the sensing device 12 from the fixed dental bridge 50. In another embodiment, as shown in FIG. 16, the dental appliance 10 may include a denture 52 including the sensor assembly 20 coupled to a denture tooth 54. In addition, in another embodiment, as shown in FIG. 17, the dental appliance 10 may include a removable partial denture 56 including the sensor assembly 20 to a denture tooth 54.

Figure 18:
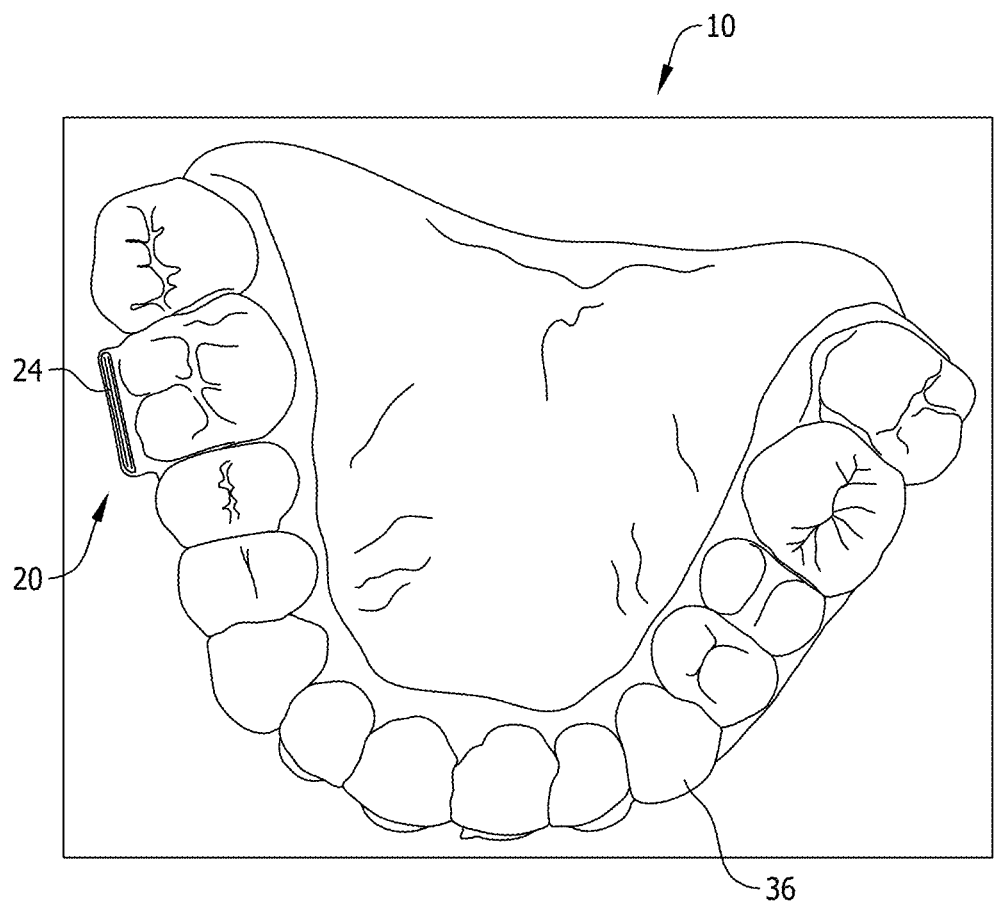
FIG. 18 is a top view of a dental appliance that may be used to support a sensing device within an oral cavity, according to an embodiment of the present invention.
Figure 19:
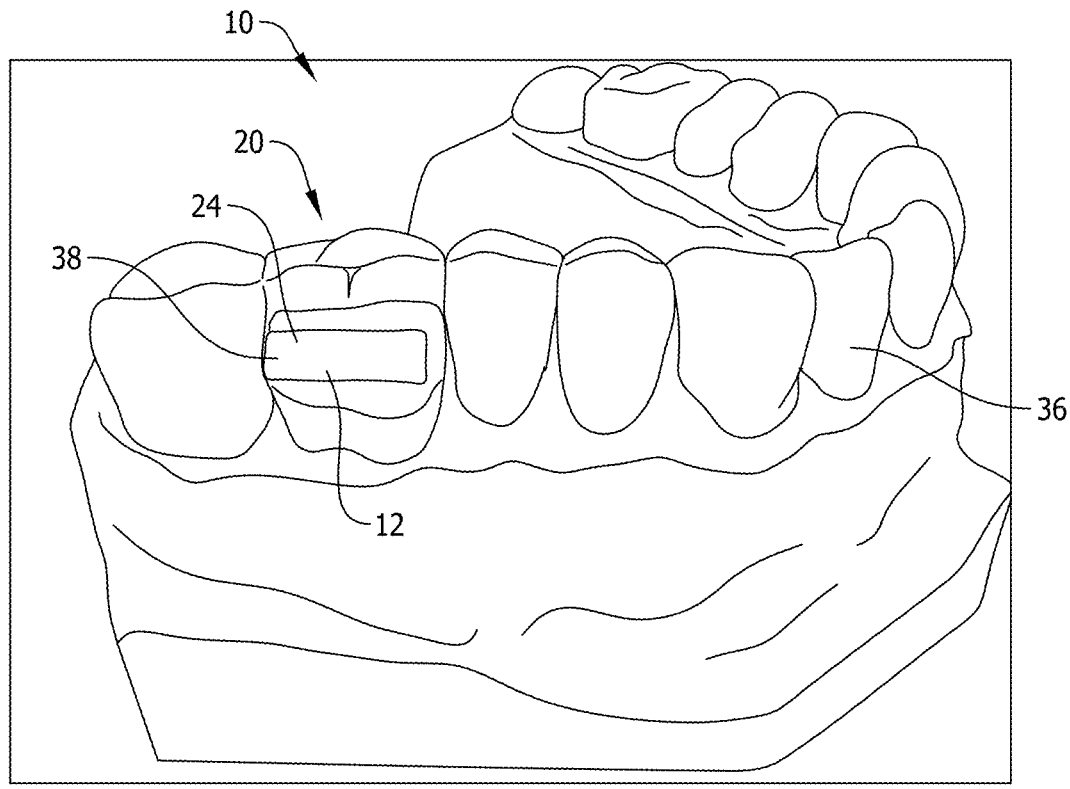
FIGS. 19-20 are perspective view of portions of the dental appliance shown in FIG. 18.
Figure 20:
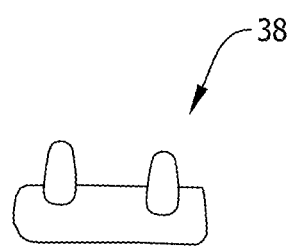

FIG. 18 is a top view of the dental appliance 10, according to another embodiment of the present invention. FIGS. 19-20 are perspective view of portions of the dental appliance 10. In the illustrated embodiment, the dental appliance 10 includes a flexible dental tray 36 and the sensor support assembly 24 is coupled to the flexible dental tray 36. The dental tray 36 is sized and shaped to cover at least a portion of the biting surface of one or more existing teeth. The dental tray 36 includes an inner surface that defines a cavity that is configured to receive at least one tooth therein. The sensor assembly 20 includes a sensor support assembly 24 that is coupled to the dental tray 36 and a sensor attachment device 38 that is removably coupled to the sensor support assembly 24. The sensor attachment device 38 is adapted to be coupled to the sensing device 12 to facilitate support the sensing device 12 from the sensor support assembly 24. In one embodiment, the inner surface of the flexible dental tray 36 includes a recessed portion that defines a cavity that is configured to receive the sensor support assembly 24 therein. In another embodiment, the sensor support assembly 24 is unitarily formed with the flexible dental tray 36 and extends outwardly from an outer surface of the flexible dental tray 36. During operation, the sensing device 12 is attached to the sensor attachment device 38, which is coupled to the sensor support assembly 24. As the patient wears the dental tray over the teeth, the sensing device 12 contacts the fluid, air, and/or material within the oral cavity.

Exemplary embodiments of a dental appliance are described above in detail. The apparatus is not limited to the specific embodiments described herein, but rather, components of the apparatus may be utilized independently and separately from other components and/or steps described herein. For example, the apparatus may also be used in combination with other dental appliance systems, and are not limited to practice with only the dental appliance system as described herein. Rather, the exemplary embodiment can be implemented and utilized in connection with many other applications.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

While the invention has been described in terms of various specific embodiments, those skilled in the art will recognize that the invention may be practiced with modification within the spirit and scope of the claims.

What is claimed is:

1. A dental appliance, comprising:
   an abutment device adapted to be coupled to a jawbone;
   a support ring configured to extend radially about an outer surface of the abutment device;
   a sensor support assembly coupled to the support ring, the sensor support assembly including a sensor chamber that is configured to receive a sensing device therein;
   a chamber cover removably coupled to the sensor support assembly to enclose the sensor chamber, the chamber cover including a plurality of orifices defined along an outer surface of the chamber cover, each of the plurality of orifices configured to couple the sensor chamber in flow communication with an oral cavity; and
   a tooth cap coupled to the abutment device, the tooth cap including:
   a contoured outer surface forming a biting surface;
   an inner surface defining a cavity that is configured to receive the abutment device such that the tooth cap extends about a perimeter of the abutment device; and
   a cap opening extending through an outer surface of the tooth cap and configured to receive the sensor support assembly therein such that an outer surface of the chamber cover is substantially flush with the outer surface of the tooth cap.

2. The dental appliance of claim 1, including at least one fastener configured to couple the chamber cover to the sensor support assembly.

3. The dental appliance of claim 1, wherein the abutment device includes a supporting ridgeline, the tooth cap including an outer ridge configured to contact the supporting ridgeline to support the tooth cap from the abutment device.

4. The dental appliance of claim 3, wherein the tooth cap is orientated between adjacent teeth.

5. The dental appliance of claim 1, wherein the sensing device includes a pH sensor.

6. The dental appliance of claim 1, wherein each of the plurality of orifices are configured to allow saliva to enter the sensor chamber from the oral cavity.

7. The dental appliance of claim 1, wherein the sensor support assembly extends radially outwardly from the support ring.

8. The dental appliance of claim 1, including a jawbone anchoring member that is adapted to be coupled to the jawbone, the abutment device removably coupled to the jawbone anchoring member and extending outwardly from the jawbone anchoring member and into the oral cavity.

9. The dental appliance of claim 1, the sensing device includes at least one of a pH sensor, a pressure sensor, a force sensor, an RFID device, and an accelerometer.

10. A dental appliance, comprising:
   an abutment device adapted to be coupled to a jawbone;
   a support ring configured to extend radially about an outer surface of the abutment device;
   a sensor support assembly extending radially outwardly from the support ring, the sensor support assembly including:
   a sensor chamber that is configured to receive a sensing device therein; and
   at least one orifice defined along an outer surface of the sensor support assembly and configured to couple the sensor chamber in flow communication with an oral cavity; and
   a tooth cap coupled to the abutment device, the tooth cap including:
   a contoured outer surface forming a biting surface;
   an inner surface defining a cavity that is configured to receive the abutment device such that the tooth cap extends about a perimeter of the abutment device; and
   a cap opening extending through an outer surface of the tooth cap and configured to receive the sensor support assembly therein such that an outer surface of the sensor support assembly substantially flush with the outer surface of the tooth cap.

11. The dental appliance of claim 10, wherein the abutment device includes a supporting ridgeline, the tooth cap including an outer ridge configured to contact the supporting ridgeline to support the tooth cap from the abutment device.

12. The dental appliance of claim 11, wherein the tooth cap is orientated between adjacent teeth.

13. The dental appliance of claim 11, wherein the outer ridge of the tooth cap is configured to be positioned below a gumline.

14. The dental appliance of claim 10, wherein the sensing device includes a pH sensor.

15. The dental appliance of claim 10, wherein the at least one orifice is configured to allow saliva to enter the sensor chamber from the oral cavity.

16. The dental appliance of claim 10, including a jawbone anchoring member that is adapted to be coupled to the jawbone, the abutment device removably coupled to the jawbone anchoring member and extending outwardly from the jawbone anchoring member and into the oral cavity.

17. The dental appliance of claim 10, the sensing device includes at least one of a pH sensor, a pressure sensor, a force sensor, an RFID device, and an accelerometer.

* * * * *